US008106242B2

(12) United States Patent
Reintjens et al.

(10) Patent No.: US 8,106,242 B2
(45) Date of Patent: Jan. 31, 2012

(54) PROCESS FOR THE PRODUCTION OF COMPOUNDS VIA HAZARDOUS INTERMEDIATES IN A SERIES OF MICROREACTORS

(75) Inventors: Rafael Wilhelmus Elisabeth Ghislain Reintjens, Etten Leur (NL); Quirinus Bernardus Broxterman, Munstergeleen (NL); Martina Kotthaus, Linz (AT); Peter Poechlauer, Linz (AT)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/301,113

(22) PCT Filed: May 23, 2007

(86) PCT No.: PCT/EP2007/004562
§ 371 (c)(1),
(2), (4) Date: Jul. 15, 2009

(87) PCT Pub. No.: WO2007/134847
PCT Pub. Date: Nov. 29, 2007

(65) Prior Publication Data
US 2010/0029990 A1    Feb. 4, 2010

(30) Foreign Application Priority Data
May 23, 2006    (EP) .................................. 06010570

(51) Int. Cl.
*C07C 209/42*    (2006.01)
*C07C 45/40*    (2006.01)
*C07C 29/132*    (2006.01)

(52) U.S. Cl. ........ 564/375; 564/489; 568/430; 568/469; 568/815; 568/909.8

(58) Field of Classification Search ........................ None
See application file for complete search history.

(56) References Cited

U.S. PATENT DOCUMENTS

| | | | |
|---|---|---|---|
| 4,351,954 A | 9/1982 | Muramatsu et al. | |
| 7,332,632 B2 | 2/2008 | Ataka et al. | |
| 2003/0233010 A1 | 12/2003 | Lee et al. | |
| 2007/0053829 A1 | 3/2007 | Sethi et al. | |

FOREIGN PATENT DOCUMENTS

| | | |
|---|---|---|
| DE | 40 00 163 | 7/1991 |
| DE | 102 57 239 B3 | 7/2004 |
| EP | 0 147 593 | 7/1985 |
| EP | 0 863 146 | 9/1998 |
| EP | 1 500 649 A1 | 1/2005 |
| EP | 1 710 223 | 10/2006 |
| GB | 709 450 | 5/1954 |
| GB | 2 113 205 | 8/1983 |
| WO | 02/072518 | 9/2002 |
| WO | WO 02/072518 | 9/2002 |
| WO | WO 03/037502 A1 | 5/2003 |
| WO | WO 2007/027785 A2 | 3/2007 |

OTHER PUBLICATIONS

Database CAPLUS on STN, Acc. No. 2004:842122, Kurihara, JP 2004285001 A, (Oct. 14, 2004) (abstract).*
International Search Report for PCT/EP2007/004562, mailed May 13, 2008.
Written Opinion of the International Searching Authority for PCT/EP2007/004562, mailed May 13, 2008.
Kawasaki, Masanori et al., "Total Synthesis of (−)-Kaitocephalin", Organic Letters, vol. 7, No. 19, (2005), pp. 4165-4167.
Bonini, Carlo et al, "Synthesis, Biological Activity and Modelling Studies of Two Novel Anti HIV PR Inhibitors with a Thiophene Containing Hydroxyethylamino Core", Tetrahedron, vol. 61, No. 27, (2005), pp. 6580-6589.
Schwarz, Jacob B. et al., "Novel Cyclopropyl .Beta.-Amino Acid Analogues of Pregabalin and Gabapentin that Target the .alpha.2-.delta. Protein", Journal of Medicinal Chemistry, vol. 48, No. 8, (2005), pp. 3026-3035.
Krawczyk, Ewa et al., "Regio- and Stereoselective Reactions Between Cyclic Baylis-Hillmann Type Adducts and N-nucleophiles and P-nucleophile", Tetrahedron, vol. 61, No. 6, (2005), pp. 1449-1457.
Pandey, Satyendra K. et al., "Enantioselective Synthesis of (−)-Galantinic Acid", Tetrahedron Letters, vol. 45, No. 30, (2004), pp. 5877-5879.
Dhavale, Dilip D. et al., "Asymmetric Dihydroxylation of D-Glucose Derived .alpha., .beta.-Unsaturated Ester: Synthesis of Azepane and Nojirimycin Analogues", Journal of Organic Chemistry, vol. 69, No. 14, (2004), pp. 4760-4766.
Hale, Karl J. et al., "A Practical New Asymmetric Synthesis of (2S, 3S)- and (2R, 3R)-3-Hydroxyleucine", Tetrahedron, vol. 50, No. 30, (1994), pp. 9181-9187.
Kasina, Sudhakar et al., "Tissue Distribution Properties of Technetium-99m-Diamide-Dimercaptide Complexes and Potential use as Renal Radiopharmaceuticals", Journal of Medicinal Chemistry, vol. 29, No. 10, (1986), pp. 1933-1940.
Rimmer, Stephen et al., "Synthesis of Telechelic Oligostyrenes by the Ozonolysis of Poly(Styrene-Stat-Butadiene): Protection of Styrene Units Against Ozone Attack by the use of Di-N-Alkyl Amides as Sacrificial Ozone Scavengers", Journal of Polymer Science, Part A: Polymer Chemistry, vol. 34, No. 17, (1996), pp. 3573-3583.
Zadok, E. et al., "Ozonolysis by Microwave Discharge of Oxygen of Naphthalene Adsorbed on Florosil", Tetrahedron Letters, vol. 25, No. 37, (1984), pp. 4175-4176.
Watts, "Continuous flow microreactors for drug discovery," Current Opinion in Drug Discovery & Development, 2004, vol. 7, No. 6, pp. 807-812, UK.

(Continued)

*Primary Examiner* — Brian J Davis
(74) *Attorney, Agent, or Firm* — Nixon & Vanderhye P.C.

(57) ABSTRACT

Multi-step process for the preparation of compounds via hazardous intermediates comprising the steps of a) preparing in a microreactor a hazardous intermediate and b) optionally performing one or more reaction steps on the hazardous intermediate in one or more additional microreactors and c) further converting the hazardous intermediate with a suitable reaction agent in a subsequent microreactor until a stable end product is formed.

16 Claims, 2 Drawing Sheets

OTHER PUBLICATIONS

Panke et al, "A Practical Approach of Continuous Processing to High Energetic Nitration Reactions in Microreactors," Synthesis 2003, No. 18, pp. 2827-2830, USA.

Saaby et al, "The use of a continuous flow-reactor employing a mixed hydrogen-liquid flow stream for the efficient reduction of imines to amines," Chemical Communications, The Royal Society of Chemistry 2005, UK.

Kirschning et al, "PASSflow Syntheses Using Functionalized Monolithic Polymer/Glass Compositions in Flow-Through Microreactors," Communications, Angew. Chem. Int. Ed. 2001, vol. 40, No. 21, DE.

* cited by examiner

PROCESS FOR THE PRODUCTION OF COMPOUNDS VIA HAZARDOUS INTERMEDIATES IN A SERIES OF MICROREACTORS

This application is the U.S. national phase of International Application No. PCT/EP2007/004562, filed 23 May 2007, which designated the U.S. and claims priority to Europe Application No. 06010570.7, filed 23 May 2006, the entire contents of each of which are hereby incorporated by reference.

FIELD

The invention relates to a multi-step process for the preparation of compounds via hazardous intermediates. The invention also relates to a reaction system comprising at least two continuous microreactors.

BACKGROUND AND SUMMARY

Many syntheses in the fine chemical and pharmaceutical industry involve the production of compounds via intermediates such as azides and peroxo compounds, which intermediates are hazardous and are therefore not very attractive from a safety point of view.

Organic amines are versatile organic compounds, and can be readily made chemically from the corresponding azides (e.g. by hydrogenation). Formation of azides as well as the handling of azides creates significant safety issues. Moreover, the organic azides itself, especially those with a high N to C ration, are intrinsically unsafe having the potential for highly exothermic decomposition (see for instance H. C. Kolb; M. G. Finn; K. B. Sharpless, Angew. Chem (2001), 40, 2021 (reference note 77) or M. Peer in Spec. Chem. (1998) 18, 256-263). During this decomposition the enormous amounts of energy liberated can cause explosions.

Organic peroxo compounds, like hydroperoxides, endoperoxides, ozonides, peroxo acids are also hazardous compounds. Organic peroxo compounds are frequently very unstable compounds, which can decompose spontaneously under explosion due to thermal or mechanical stress; for example by shock, impact, friction or by catalytic effect of impurities, which decomposition causes a(n) (large) explosion.

Although hazardous, such compounds are very interesting intermediates in the production of for example alcohols, aldehydes and acids.

So, although desired from a syntheses point of view, production, isolation and storage of hazardous intermediates such as organic peroxo compounds and organic azides is less desirable from a safety point of view.

For this reason it was the aim of the present invention to find a process for the production of compounds such as amines, alcohols, aldehydes and acids via hazardous intermediates and/or hazardous reaction conditions, which reduces safety concerns and the existence of hazardous conditions, avoiding the danger of explosions while maintaining efficiency and ease of operations.

This aim was solved according to the invention by a multi-step process, where a reactive intermediate—e.g. an organic azide or peroxo compound—is produced in a microreactor and then without isolation converted in a subsequent microreactor into the stabile product, optionally with additional intermediate conversions on the reactive intermediate.

DETAILED DESCRIPTION OF EXEMPLARY EMBODIMENTS

Subject matter of the application is therefore a multi-step process for the preparation of compounds via hazardous intermediates comprising the steps of
 a) preparing in a microreactor a hazardous intermediate and
 b) optionally performing one or more reaction steps on the hazardous intermediate in one or more additional microreactors and
 c) further converting the hazardous intermediate with a suitable agent in a subsequent microreactor until a stable end product is formed.

The conversion in step c) may for example be a reduction reaction of the hazardous intermediate whereby the hazardous intermediate is reduced using a reducing agent.

With the process of the present invention, the hazardous intermediate is directly converted, without isolation, into a stable and hence less dangerous product. Therefore, the process of the present invention reduces safety concerns and minimizes the existence of hazardous conditions. So with the process of the invention, the danger of explosion is eliminated or at least the risks of explosions are drastically reduced. An additional advantage of the process of the invention is that it is an efficient process that is easy to operate.

In step a) of the present invention a hazardous intermediate is prepared in a microreactor.

The hazardous intermediate is preferably selected from the group consisting of organic azides and organic peroxo compounds.

1. Azide Intermediates:

For preparing an organic azide as hazardous intermediate an organic compound suitable to react with $N_3^-$, is used as starting compound and reacted with $N_3^-$ The introduction of the azido function can take place for example by addition of the azide reagent to a suitable unsaturated organic compound, or by substitution of a leaving group, e.g. a halogen atom, a hydroxy-group, optionally activated in situ with diethyl azodicarboxylate/triphenylphosphine (Mitsunobu conditions), an acyloxy-group, or a sulfonyloxy function in an organic compound suitable for reaction with $N_3^-$, or by ring opening of optionally substituted oxiranes or aziridines.

Azide Reagents:

$N_3^-$ may be used in any form known to the person skilled in the art. For example, the azido function may be introduced using an azide reagent selected from the group consisting of $HN_3$; alkali azides like $NaN_3$, $LiN_3$ and $KN_3$; quarternary ammonium azide, like tetrabutylammonium azide; azido-trimethyl-silan; halogen azides, like chloro-, bromo- or iodo azide; and the like. Optionally, also a proton source is present during the reaction with $N_3^-$. Examples of proton sources include ammonium chloride.

Preferred azide reagents are alkali azides like $NaN_3$, $LiN_3$ and $KN_3$, which may optionally be combined with ammonium chloride.

Substrates:

Suitable substrates for the introduction of the azide function by substitution are organic compounds of the general formula R-L, wherein R stands for an optionally substituted alkyl group and L is a leaving group.

The alkyl group may be linear, branched or cyclic and preferably has 1 to 20 C-atoms. The chain may also include one or more heteroatoms selected from the group consisting of N, S and O.

Suitable examples of a leaving group L include a halogen atom, like Cl, Br or I; a hydroxy-group, optionally activated in situ with diethyl azodicarboxylate/triphenylphosphine (Mitsunobu conditions); an acyloxy-group; or a sulfonyloxy-group, like trifluormethansulfonyloxy, methanesulfonyloxy, benzenesulfonyloxy, p-toluenesulfonyloxy or m-nitrobenzenesulfonyloxy. Preferably the leaving groups L in R-L are halogen, for example Cl or Br, or sulfonyloxy-groups.

Suitable substrates for the introduction of the azide function by ring-opening are optionally substituted organic compounds containing an oxirane or aziridine.

Especially interesting are enantiomerically enriched substrates in which a halogen atom, a hydroxy-group or a sulfonyloxy-group can be substituted by azide with inversion of configuration, or enantiomerically enriched substrates in which an oxirane or aziridine that can be stereoselective and regioselective ring-opened by azide. For example, the stereo- and regioselective oxirane ring-opening of ethyl (3R,4S,5S)-4,5-epoxy-3-(1-ethylpropoxy)-cyclohex-1-ene-1-carboxylate with sodium azide.

Suitable substrates for the introduction of the azide function by addition reaction are optionally substituted unsaturated organic compounds, for example optionally substituted alkenes or alkynes. A specific class of alkenes are those having an electron-withdrawing substituent, like a nitrile, carboxylic acid ester, nitro, ketone or aldehyde group, susceptible for 1,4-addition of alkali azides.

These organic compounds may be linear, branched or cyclic with 2 to 30 C-atoms in the chain, may contain a combination of reactive functions and may also include one or more heteroatoms selected from the group consisting of N, S and O.

Substituents:

The organic compounds may optionally be substituted with one or more substituents preferably selected from the group consisting of an optionally substituted $C_1$-$C_6$-(cyclo)alkyl, $C_1$-$C_6$-(cyclo)alkenyl, $C_1$-$C_6$-(cyclo)alkynyl, an optionally substituted $C_1$-$C_{10}$-(hetero)aryl, an amine, acylamido, nitro, carboxylic acid, carboxylic acid ester, carboxamide, nitrile, an oxo group, like an aldehyde or a ketone, a hydroxy, an alkoxy group, and the like.

The organic compounds may further be fused with an optionally substituted alkane ring, $C_5$-$C_{20}$-aryl or $C_4$-$C_{20}$-heteroaryl compounds.

Examples of suitable substituents for the alkenyl, alkynyl and/or (hetero)aryl groups include the above mentioned substituents and halogen atoms.

Examples of suitable organic compounds include 4-methyl-pent-3-en-2-one, acrolein, 2-methyl-2-pentene, cyclohexen-2-enone, 5-cholestene, 2-isopropenyl-5-methyl-cyclohexanol, cyclohexene-epoxide, styrene epoxide, ethyl(3R,4S,5S)-4,5-epoxy-3-(1-ethylpropoxy)-cyclohex-1-ene-1-carboxylate, ethyl(3R,4R,5R)-4,5-imino-3-(1-ethylpropoxy)-cyclohex-1-ene-1-carboxylate, 1-phenylethanol, 1-phenylethanol p-tosylate ester, 3-phenyl-propan-1 ol-mesylate ester, 4-phenylbutan-2-ol mesylate ester, (1-bromo-ethyl)benzene, (1-chloro-ethyl)benzene.

Reaction Conditions:

The addition reaction may be performed in a single solvent such as water; DMF; NMP; DMSO; DMA; alcohols, for example methanol, ethanol, iso-propanol; hydrocarbons, for example heptane; toluene; ethers, for example tetrahydrofuran, dioxan, methyl-tert.-butyl ether (MTBE) or ethyl-tert.butyl ether (ETBE); ketons, for example methyl ethyl keton (MEK) or methyl-isobutyl keton (MIBK); chlorinated solvents, for example chloroform or methylenechloride; acetonitrile; or may be performed in a combination of miscible solvents from the list above, for example water-methanol or the like; or in a two phase combination of a water-immiscible organic solvent mentioned above and water, optionally combined with a suitable phase transfer catalyst, like tetraalkylammonium or tetraalklyphosphonium halides.

The reaction temperature depends on the selected substrates, solvents and azide reagents and can vary from 0 to 200° C. Preferably the azidation reaction is performed at higher temperatures between 50-150° C.

Surprisingly, high reaction temperatures can be use for the azide substitution reaction that are significantly close to the decomposition temperature. Similar conditions in a batch or semi-batch process may lead to considerable side-product formation or uncontrolled decomposition leading to explosion.

To the ring-opening reaction of epoxides or aziridines with azide a suitable proton source can be added, such as ammonium chloride.

The addition reaction to alkenes and alkynes and ring-opening reaction of epoxides or aziridines can be accelerated by adding a Lewis acid to the reaction system.

Suitable Lewis acids preferably are for example trifluoroborane, aluminum-, zinc and titanium(IV)-chloride.

Further examples of suitable azide donors, substrates, leaving groups and reaction conditions (solvents, temperature, catalysts and the like) are described for example by E. F. C. Scriven and K. Turnbull in Chem. Rev. (1988), 88, 297-368.

The so produced azide intermediates need not be isolated in pure form and can be directly transferred from the crude form to the desired stable end product in one or more subsequent microreactor systems, optionally with additional intermediate transformation reactions.

Optionally, additional transformations on the hazardous intermediates can be done in one or more intermediate microreactor systems (step b) before the hazardous intermediate is reduced to a stable end product (step c).

For example, additional transformations on an hazardous intermediate can be found for the preparation of oseltamivir phosphate (Tamiflu®) as described by J. C. Rohloff et al in J. Org. Chem. (1998), 63, 4545-4550. By reaction of ethyl (3R,4R,5R)-4,5-imino-3-(1-ethylpropoxy)-cyclohex-1-ene-1-carboxylate with sodium azide the hazardous intermediate ethyl (3R,4R,5S)4-amino-5-azido-3-(1-ethylpropoxy)-cyclohex-1-ene-1-carboxylate is formed which is first acylated with acetic acid anhydride to the 4-acetamido analogue before reduction of the azido functionality.

2. Peroxo Intermediates:

In a second embodiment, the reactive and explosive intermediate is a peroxo compound, like an organic peroxide R—OO—R or organic hydroperoxide R—OOH.

In the first process step the intermediate organic peroxide or hydroperoxide can be prepared for example by the following reactions:

reaction of an alkyl halide, alkyl sulfate or alkyl sulfonate with hydrogen peroxide under basic conditions reaction of an alkyl halide, alkyl sulfate or alkyl sulfonate with sodium peroxide (R—OO—R)

reaction of an organometallic compound (for example, R—MgX, R—Li) with oxygen reaction of an alkane having a reactive C—H with oxygen (autoxidation)

reaction of an alkene with singlet oxygen reaction of a diene with singlet oxygen (cyclic peroxide)

reaction of an alkene or aromatic compound with ozone in a solvent

Preferred reaction types are the reaction of an alkene or aromatic compound with ozone in a solvent, the reaction of an alkane having a reactive C—H with oxygen, or the reaction of an alkene with singlet oxygen.

Suitable alkenes or aromatic compounds for the reaction with ozone or with singlet oxygen are optionally substituted unsaturated organic compounds. These organic compounds may be linear, branched or cyclic with 2 to 30 C-atoms in the chain, may contain a combination of reactive functions and may also include one or more heteroatoms selected from the group consisting of N, S and O.

Substituents:

The organic compounds may be optionally substituted with one or more substituents selected from the group consisting of optionally substituted $C_1$-$C_6$-(cyclo)alkyl, $C_1$-$C_6$-(cyclo)alkenyl, $C_1$-$C_6$-(cyclo)alkynyl, an optionally substituted $C_1$-$C_{10}$-(hetero)aryl, an amine, acylamido, nitro, carboxylic acid, carboxylic acid ester, carboxamide, nitrile, an oxo group, an aldehyde, a hydroxy, an alkoxy group, and the like.

Examples of suitable substrates include naphthalene, furane, butadiene, cyclohexene, cycloocten, cyclooctadien, vinyl pyridine, methyl methacrylate, maleic acid anhydride, pinene, α-terpinene, citronellol, isopropylbenzene.

Singlet oxygen can be generated in a photochemical method by irradiation of molecular oxygen in the presence of a photosensitizer. Singlet oxygen can also be generated by non-photochemical methods as for example from hydrogenperoxide and NaOCl or sodium molybdate, or from ozone and $(PhO)_3P$.

Ozone can be generated by electric discharge, photochemically (UV) or electrolysis as described in Kirk-Othmer Encyclopedia of Chemical technology, Wiley&Sons, 2005, vol 17, 793-801.

Surprisingly ozonolysis can also be performed in combustible solvents and in solvent mixtures like for example an alcohol/acetate mixture.

Examples for further suitable substrates, reagents and reaction conditions (solvents, temperature, catalysts and the like) are described for example R. Hiatt in: Organic Peroxides, Vol 2, D. Swern (Ed.), Wiley-Interscience, New York, 1971, page 1-151 or Houben-Weyl, Methoden der Organischen Chemie, 4.Auflage, E13.

The so produced peroxo intermediates need not be isolated or purified and can be directly transferred from the crude form to the desired stable end product in one or more subsequent microreactor systems, optionally with additional intermediate transformation reactions.

Optionally, additional transformations on the hazardous intermediates can be done in one or more intermediate microreactor systems (step b) before the hazardous intermediate is reduced to a stable end product (step c).

In step c) the formed hazardous intermediate is reduced with a suitable reducing agent in a subsequent microreactor system.

In case of an azide intermediate this is done by reducing the formed organic azide by catalytic hydrogenation or by reduction with a suitable reducing agent into a stable amine.

Suitable reducing agents include hydrogen gas or formic acid, optionally as mixtures with substituted amines like triethylamine or hydrazine in the presence of a preferably immobilized heterogeneous hydrogenation catalyst, hydride reducing reagents like $NaBH_4$, $LiAlH_4$, or reduction with diimide, or reduction with a suitable trialkyl- or triarylphosphine, like trimethylphosphine or triphenylphosphine (Staudinger reaction).

Suitable heterogeneous hydrogenation catalysts include for example Pd(Pd(OH)$_2$, Pd/C, Pd/BaSO$_4$, Pd/CaCO$_3$, Pd/Al$_2$O$_3$, etc), Pt, Raney Ni, Ru, and the like.

The reduction is preferably performed in the organic solvent used in the first step, or in case of a two-phase system in the organic solvent phase containing the organic azide intermediate.

The hydrogenation pressure is 0.05-10 MPa, preferably 0.1-0.5 MPa, the reaction temperature is in a range from 10 to 100° C., preferably 15 to 60° C.

Further examples for reaction conditions (solvents, temperature, catalysts and the like) are described for example in E. F. C. Scriven and K. Turnbull, Chem. Rev. (1988), 88, 297-368.

In case of a peroxo intermediate the organic peroxide or hydroperoxide may be reduced into a stable end product (alcohol, aldehyde or ketone) preferably by:

hydrogenation in the presence of a suitable heterogeneous catalyst (Raney Ni, Pd—C, Pd—BaCO$_3$, Pt, PtO$_2$, etc.)

hydride reduction using $NaBH_4$ of $LiAlH_4$ or the like by metal reduction (for example: Na/ROH, Zn/AcOH)

reduction with phosphine (for example: Ph$_3$P, Et$_3$P, n-Bu$_3$P) or trialkylphosphite (for example: (MeO)$_3$P, (EtO)$_3$P)

reduction with hydrazine ($N_2H_4$ or $N_2H_4.H_2O$)

reduction with diimide (HN=NH)

bisethanolsulfid

The reduction is preferably performed in the organic solvent used in the preceding step a) and/or b), or in case of a two-phase system in the organic solvent phase containing the organic peroxo intermediate.

In case of hydrogenation the reaction pressure is for example 0.05-10 MPa, preferably 0.1-0.5 MPa, the reaction temperature is in a range from 10 to 100° C., preferably 15 to 60° C.

Further examples for reaction conditions (solvents, temperature, catalysts and the like) are described for example Houben-Weyl, Methoden der Organischen Chemie, 4.Auflage, E13.

Examples of hydroperoxide reduction are given for instance in the book Comprehensive Organic Transformations (second edition) by R. C. Larock, Wiley-VCH, New York, 1999, page 1073-1075.

Preferably, all steps of the process of the invention are done in subsequent microreactors so that the process can be performed in a safe way because of low hold-up of the reactive/hazardous intermediate. Further advantage of such a process is the increased productivity/yield as a result of the direct conversion of unstable intermediates.

In a preferred embodiment, the invention relates to a process for the preparation of compounds via hazardous intermediates comprising the steps of
  a) reacting in a first continuous microreactor an organic compound suitable for reacting with $N_3^-$, with $N_3^-$ under formation of the corresponding organic azides
  b) optionally performing one or more reaction steps on the organic azide in one or more additional microreactors and c) further reducing the formed organic azide with a suitable reducing agent in a second continuous microreactor to form an amine.

This preferred embodiment of the process of the invention is preferably used for the preparation of R—NH$_2$, wherein the reactive and explosive intermediate R—N$_3$ is directly converted into the desired product.

This has as the main advantage that there is no build-up of R—N$_3$ during the process and no storage of organic azides is needed, which is highly advantageous from a safety point of view.

In another preferred embodiment, the invention relates to a process for the preparation of compounds via hazardous intermediates comprising the steps of a) reacting in a first continuous microreactor an organic compound suitable for reacting with hydrogenperoxide, ozone or (singlet) oxygen, with hydrogenperoxide, ozone or (singlet) oxygen under formation of the corresponding organic peroxide or hydroperoxide and b) optionally performing one or more reaction steps on the organic peroxide or hydroperoxide in one or more additional microreactors and c) further reducing the formed peroxides with a suitable reducing agent in a second continuous microreactor to form a stable alcohol, or a stable aldehyde or ketone, optionally protected as the hydrate, hemiacetal or acetal.

This second preferred embodiment of the process of the invention, is a process for the preparation of alcohols (R—OH), aldehydes (R—CHO) or ketones, optionally protected as the hydrate, hemiacetal or acetal, wherein the reactive and explosive intermediate organic peroxides R—OO—R or organic hydroperoxides R—OOH are preferably directly converted into the desired product. This has as the main advantage that there is no build-up of R—OO—R or R—OOH, which is highly advantageous from a safety point of view. All steps of the process of the invention are performed in a microreactor.

Most preferably step c) for both cases consists of a hydrogenation step.

Figure 1:
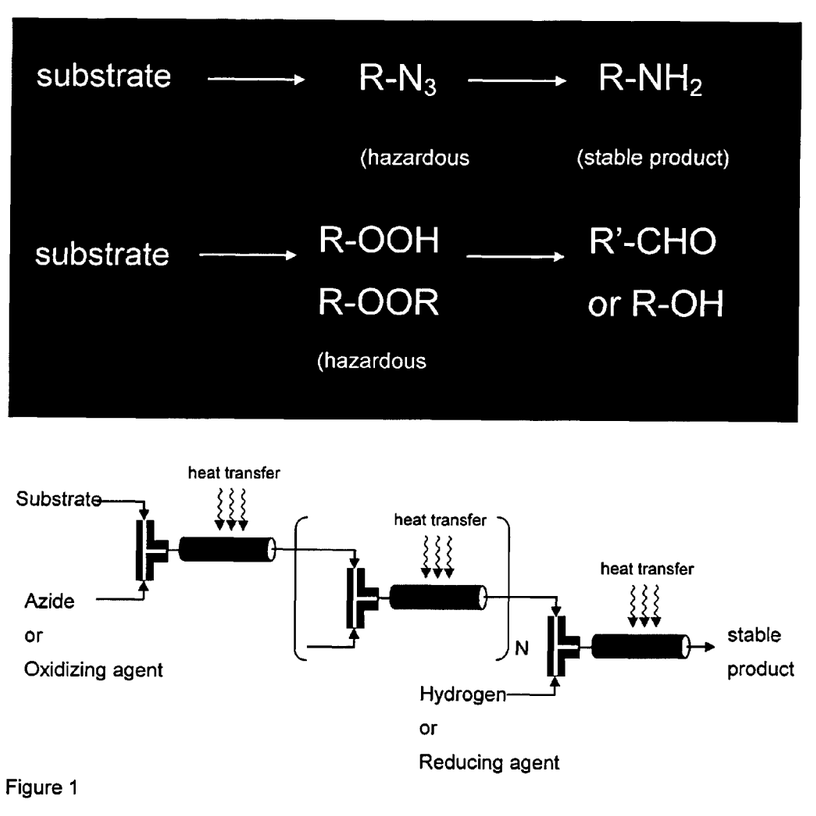
FIG. 1 shows a general reaction of suitable substrates with azide or ozone and subsequent hydrogenation of the hazardous intermediates, with optional additional intermediate transformation reactions and an exemplary reactor set-up to accomplish the same.

FIG. 1 shows the general reaction of suitable substrates with azide or ozone and subsequent hydrogenation of the hazardous intermediates, with optional additional intermediate transformation reactions, but is not meant to limit the invention in any way.

Step a), optional step b) and step c) are all performed in microreactors, which means that a micro structured reactor is applied in subsequent reaction steps until a safe product or intermediary is obtained.

The phase containing the reactants for each reaction step may be multi-phasic (liquid/liquid immiscible or gas/liquid) or homogeneous liquids (miscible) or gases. The choice of micro structured reactors can be adapted to the specific situation per reaction step.

As used herein, microreactor means micro- and minireactors, which differ only form conventional size reactors by reason of the dimensions and constructions of the reaction channel structures.

A microreactor is generally defined as a miniaturized reactor with characteristic dimensions (channel or plate width) in micrometers to millimeters (preferably from 0.01 mm to 10.0 mm). A number of microreactors may be combined in parallel to form a micro-stuctured reactor. Thus, the volume, available for reaction depends on the diameter and length of the microreactor, or in case a micro-stuctured reactor is used on the dimension of the parallel channels and the number of parallel channels. The volume of micro-reactors or micro-structured reactors typically lies in the range of 1 ml to 1 m$^3$, preferably from 10 ml to 50 ltr. Preferably, a microreactor is defined as a reactor having a channel with a hydraulic diameter of 20 mm or less. The hydraulic diameter $D_h$ is defined as 4 A/U, wherein A is the cross sectional area of the reactor channel and U is the perimeter of said cross section.

For a round tube, the hydraulic diameter $D_h$ equals the diameter of the tube. For a rectangular duct, that has a cross section with a rectangular shape, the hydraulic diameter equals 4 LW/2(L+W), wherein L is the length of the longest side of the rectangle and W is the width of the rectangle. For the special case of a square duct, the hydraulic diameter $D_h$ equals L.

For an annulus, the hydraulic diameter is $D_h=(4.0.25 \pi(D_o^2-D_i^2))/(\pi(D_o-D_i)=D_o-D_i$, wherein $D_o$ is the outer diameter of the annulus and $D_i$ is the inner diameter.

However, it should be noted that the general formula 4 A/U, wherein A is the cross sectional area of the reactor channel and U is the perimeter of said cross section, allows calculation of the hydraulic diameter for any shape of reactor channel.

The microreactor used in the process according to the invention, are suitable for continuous processes.

In the context of this invention, a continuous microreactor is defined as a microreactor suitable for use in a continuous process. A continuous process is defined as a method of manufacturing in which new materials are added and products removed continuously at a rate that maintains the reaction volume at a specific level. In other words, continuous reactors are reactors that may be used to carry out steady state operations.

The reaction set-up to be used in the process according to the invention comprises two or more miniaturized reactors with discrete flow passages for receiving liquid and/or gaseous chemical reactants (pure or diluted).

The micro reactor consists of a device allowing the reactants (gaseous or liquid) to enter and continuously flow through. The reactants are contacted with each other in the device, allowing a chemical reaction to take place in a narrow confined space like a channel or between two plates. One (in the case of plates) or two (in case of channels or grooves) dimensions of the micro reactor are chosen in such a way that the characteristic times for heat transfer and/or mass transfer are very low. Herewith high rates of reaction and heat transfer can be handled in a controlled fashion. The heat is transferred to or from a heat transfer fluid that does not come into contact with the reactants or the products. The walls of the micro reactor may contain catalytic activity. A (bio)catalyst may be deposited, immobilized or coated on the wall.

A number of micro reactors may be combined in parallel to form a micro structured reactor. Entering reactants are distributed over manifold systems or other distribution systems to the individual micro reactors.

Each micro-structured reactor may include mixing zones to mix the entering reactants and/or the reaction medium.

Each micro-structured reactor may contain residence zones to allow the reaction medium to obtain sufficient conversion.

The micro-structured reactor may be constructed of, or may contain, a number of parallel sub-units (mixing zones with residence zones) in a numbering-up concept to obtain sufficient production capacity. Such as in a multi channel monolith reactor for example.

Suitable devices (microreactors, micromixers, micro-heat-exchangers and the like) have been developed for example in Germany (i.e.: IMM, Mainz, and Forschungszentrum Karlsruhe) and in the USA (i.e.: MIT and DuPont).

The invention also related to a reaction system comprising at least two continuous microreactors, wherein the first microreactor is suitable for liquid/liquid or gas/liquid reactions and wherein a second microreactor is suitable for gas/liquid reactions.

It will be understood that the reaction system can also comprise instead of a first and second continuous microreactor, a first and second continuous micro-structured reactor, wherein the first micro structured reactor is suitable for liquid/liquid or gas/liquid reactions and wherein a second microreactor is suitable for gas/liquid reactions.

Liquid/liquid or gas/gas reactions are preferably performed in multi channel micro structured reactors, such as for example a monolith reactor, a HEX reactor or a printed circuit heat exchange reactor. The channel hydraulic diameter is preferably between 0.01 and 10 mm, more preferably between 0.1-1 mm. The liquid flow may be a one phase or a multi phase system. The length of the channels depends on the desired residence time, which may vary for example from 0.01 sec to 1000 sec, and is preferably between 1 sec and 100 sec.

Liquid/gas reactions may be performed in several types of micro structured reactors that provide sufficient mass transfer area between the two phases. Examples of such reactors include multi channel reactors, micro falling film reactors, micro bubble column reactors.

In another preferred embodiment of the invention, the process comprises the steps of a) reacting in a first continuous micro reactor system an organic compound suitable for reacting with $N_3^-$, with $N_3^-$ under formation of the corresponding organic azides and b) directly further reducing the formed organic azide with a suitable reducing agent (more preferably by catalytic hydrogenation) in a second continuous micro reactor system to form a stable amine, wherein step a) can be preferably performed in a continuous micro reactor suitable for homogeneous solution or two phase liquid/liquid flow, as for example a multi channel micro reactor.

and step b) can be preferably performed in a continuous gas/liquid micro reactor.

The gas/liquid micro reactor for step b) is preferably used with an immobilized catalyst.

As for example the walls of the gas/liquid micro reactor may contain catalytic activity, with the catalyst for example be deposited, immobilized or coated on the wall.

In yet another aspect of the invention, the process comprises the steps of a) reacting in a first continuous micro reactor system an organic compound, suitable for reacting with hydrogenperoxide, ozone or (singlet) oxygen, with hydrogenperoxide, ozone or (singlet) oxygen under formation of the corresponding organic an organic peroxide or hydroperoxide and b) directly further reducing these hazardous intermediates with a suitable reducing agent in a second continuous microreactor system to form a stable alcohol, or a stable aldehyde or ketone, optionally protected as the hydrate, hemiacetal or acetal, wherein step a) can be preferably performed in a continuous gas/liquid microreactor (ozone, singlet oxygen) as for example a multi channel reactor, micro falling film reactor or a micro bubble column reactor or in a continuous homogeneous solution or two phase liquid/liquid microreactor (hydrogenperoxide) as for example a multi channel reactor.

Step b) can be done analogous to the reduction to the amine.

Due to the improved heat and mass transfer the reaction rate will be much faster in the micro (structured) reactor, therefore the process conditions vary from the normally applied conditions.

Example 1

| | P and T range preferred | P and T range possible |
|---|---|---|
| Azidation | 1-50 bar | 0.5-300 |
| | 50-150° C. | 0-200° C. |
| Azide hydrogenation | 1-50 bar | 0.5-300 |
| | 50-150° C. | 0-200° C. |
| Ozonolysis | 0.5-50 bar | 0.1-100 bar |
| | −30-50° C. | −40-200° C. |
| Hydroperoxide hydrogenation | 1-50 bar | 0.5-300 |
| | 50-150° C. | 0-200° C. |

Example 1

Step a) Azidation

Sodiumazide was dissolved in water at room temperature to give an azide solution containing 3.45% w/w $NaN_3$ (density 1.017). 3-Phenylpropan-1-ol mesylate ester (95% pure) was dissolved in N-methylpyrrolidone at room temperature to give a substrate solution containing 6.33% w/w (GC analysis) 3-phenylpropan-1-ol mesylate ester (density 1.033).

Figure 2:
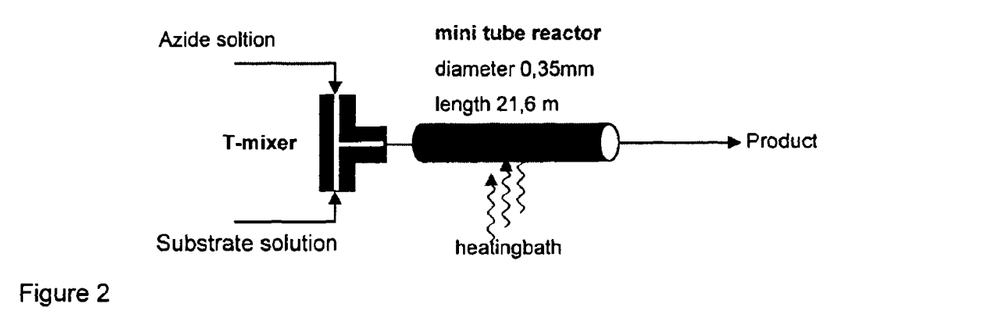
FIG. 2 shows the reactor set-up employed in Example 1 below.

The reactor set-up comprised of a T-mixer and a subsequent mini tube-reactor with an internal diameter of 0.35 mm and a length of 21.6 m (volume 2.07 ml). The T-mixer and reactant pumps were at room temperature. The mini tube-reactor was placed in an oilbath. The product coming out of the reactor was cooled and collected. Samples were analysed with GC and HPLC.

See FIG. 2

At the start of the experiment the azide pump and substrate pump were started. Molar ratio sodium azide:substrate=1.02 (slight excess azide). The oil bath temperature was 111-113° C. during the experiment.

0.301 ml/min azide solution
0.519 ml/min substrate solution
Residence time 2.5 min After 30 minutes the sample collection started, after 60 minutes the sample collection was stopped. The sample contained 0.22 m % unconverted 3-phenylpropan-1-ol mesylate ester and 2.2% w/w 3-phenyl-1-propylazide.

Conversion 95%
Selectivity 76%

Example 2

Step b) Hydrogenation

The reaction product of the continuous azidation was diluted with N-methyl pyrrolidone from 2.2% w/w to a 0.93% w/w 3-phenyl-1-propylazide solution, as substrate solution for the hydrogenation.

Figure 3:
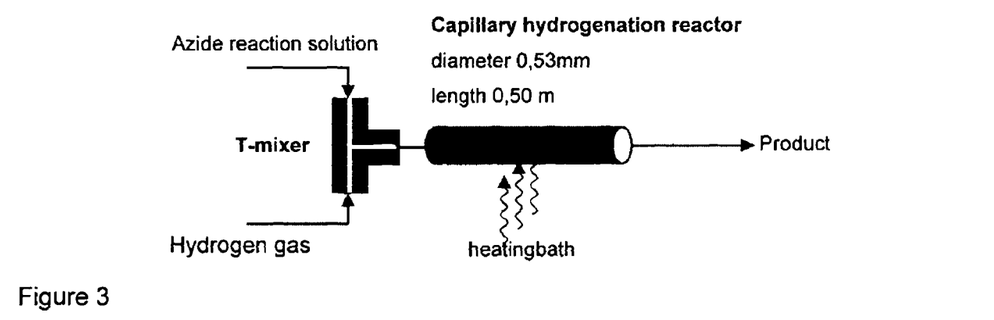
FIG. 3 shows the reactor set-up employed in Example 2 below.

The reactor set-up comprised of a T-mixer and a subsequent capillary-reactor with an internal diameter of 0.53 mm and a length of 0.50 m. The capillary reactor had a fused silica wall that was coated with a 6 micron porous alumina layer.

This alumina layer contained palladium crystallites (11 nm) as catalytic active material. The T-mixer and reactant pump were at room temperature. The capillary-reactor was placed in a waterbath at 26° C.

Substrate solution was pumped into the T-mixer with a flow of 0.20 ml/min. Hydrogen gas was fed into the T-mixer with a flow of 0.50 ml/min (1 bar). The T-mixer produced a taylor flow regime (liquid slugs). The product coming out of the reactor was collected. Samples were analysed with GC and HPLC.

See FIG. 3.

The collected product contained 0.48% w/w 3-phenyl-1-propylazide and 0.42% w/w 3-phenyl-1-propylamine. Conversion 48%, selectivity 100%.

Example 3

Ozonolysis

A falling film microreactor, as detailed in the table 2, was used for the ozonolysis of naphthalene. The liquid layer consisted in a 2% w/w naphthalene solution. Mainly methanol, butylacetate or mixtures of them were used as solvent (table 1). The gas stream for the ozonolysis was oxygen gas enriched with ozone ($O_3$-content: 130 g/NL, flow rate: 1 NL/min). (normal-liter: 1 ltr at 1 bar 20° C.)

At the beginning of the experiment the naphthalene solution was pumped with a flow rate of 2 g/min into the reactor under nitrogen atmosphere. After switching to oxygen, the gas was compressed up to 4 bar with a compressor, which was especially designed for ozone compression. Finally the ozone generator is switched on and the $O_3$-content is regulated. After 10 min all parameters showed constant values and the produced peroxides could be collected. To obtain analytic samples, small amounts of the reaction mixture were directly reduced with a solution, containing 30% w/w of bis(2-ethanol)sulfide in ethyl acetate. Quantitative GC-analysis showed the following results.

TABLE 1

| Solvent | Conversion of naphthalene [%] | Yield of OPA [%] | Selectivity [%] |
|---|---|---|---|
| methanol | 53.6 | 32.3 | 60.3 |
| butylacetate | 68.3 | 38.1 | 55.8 |
| 5% methanol in butylacetate | 52.1 | 49.9 | 95.8 |

The stable end product is o-phthalaldehyde (OPA)

TABLE 2

| Data of the falling film micro reactor: | | |
|---|---|---|
| Headspace | Width [mm] | 26 |
| | Height [mm] | 7 |
| | Length [mm] | 75 |
| | Hold-up [ml] | 13.6 |
| Microstructured plate | Channel Width [mm] | 0.6 |
| | Channel depth [mm] | 0.2 |
| | Channel length [mm] | 75 |
| | Number of channels | 32 |

Example 4

Hydrogenation of Organic Hydroperoxide

Figure 4:
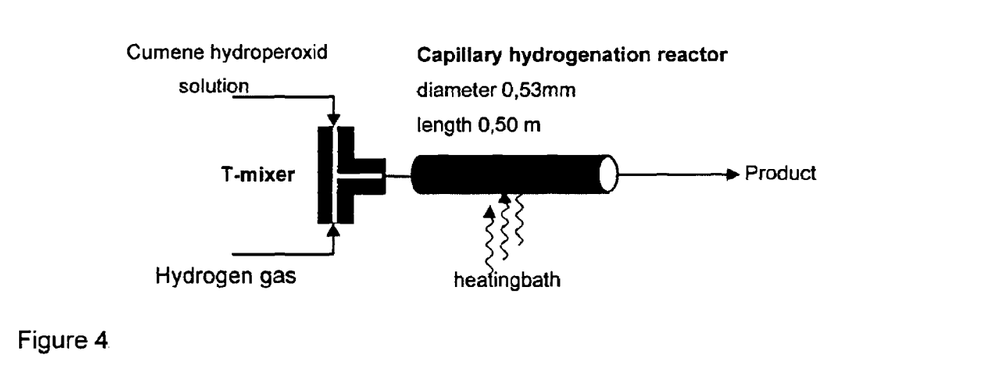
FIG. 4 shows the reactor set-up employed in Example 3 below.

Cumene hydroperoxide was dissolved in ethanol at room temperature to give a solution containing 1.035% w/w hydroperoxide. The reactor set-up comprised of a T-mixer and a subsequent capillary-reactor with an internal diameter of 0.53 mm and a length of 0.50 m. The capillary reactor had a fused silica wall that was coated with a 6 micron porous alumina layer. This alumina layer contained palladium crystallites (11 nm) as catalytic active material. The T-mixer and reactant pump were at room temperature. The capillary-reactor was placed in a waterbath at 22° C.

Cumene hydroperoxide solution was pumped into the T-mixer with a flow of 0.250 ml/min. Hydrogen gas was fed into the T-mixer with a flow of 0.600 ml/min (1 bar). The T-mixer produced a taylor flow regime (liquid slugs). The product coming out of the reactor was collected. Samples were analysed with GC and HPLC. A conversion of 73% with >99% selectivity was obtained towards 2-phenyl-2-propanol.

See FIG. 4.

The invention claimed is:

1. A multi-step process for the preparation of an amine compound via a hazardous organic azide intermediate, comprising the steps of:
   a) reacting $N_3^-$ in a continuous microreactor with an organic compound suitable for reaction with $N_3^-$ to form a corresponding organic azide,
   b) optionally performing one or more reaction steps on the organic azide in one or more additional microreactors, and
   c) further reducing the organic azide with a suitable reducing agent in a subsequent continuous microreactor to form an amine compound.

2. A multi-step process for the preparation of an amine compound via a hazardous organic azide intermediate, comprising the steps of:
   a) reacting $N_3^-$ in a first continuous microreactor with an organic compound suitable for reacting with $N_3^-$ to form a corresponding organic azide, and
   b) directly further reducing the formed organic azide with a suitable reducing agent in a second continuous microreactor to form an amine compound.

3. A multi-step process for the preparation of alcohol, aldehyde or ketone compounds, optionally protected as the hydrate, hemiacetal or acetal, via hazardous organic peroxide or hydroperoxide intermediates, comprising the steps of:
   a) reacting in a continuous microreactor an organic compound suitable for reacting with hydrogen peroxide, ozone or (singlet) oxygen, with hydrogen peroxide, ozone or (singlet) oxygen to form a corresponding hazardous organic peroxide or hydroperoxide intermediate,
   b) optionally performing one or more reaction steps on the hazardous organic peroxide or hydroperoxide intermediate in one or more additional microreactors, and
   c) further reducing the hazardous organic peroxide or hydroperoxide intermediate with a suitable reducing agent in a subsequent continuous microreactor to form a stable alcohol, or a stable aldehyde or ketone compound, optionally protected as the hydrate, hemiacetal or acetal.

4. A multi-step process for the preparation of alcohol, aldehyde or ketone compounds, optionally protected as the hydrate, hemiacetal or acetal, via hazardous organic peroxide or hydroperoxide intermediates, comprising the steps of:
   a) reacting in a continuous microreactor an organic compound suitable for reacting with hydrogen peroxide, ozone or (singlet) oxygen, with hydrogen peroxide, ozone or (singlet) oxygen to form a corresponding hazardous organic peroxide or hydroperoxide intermediate, and
   b) directly further reducing the hazardous organic peroxide or hydroperoxide intermediate with a suitable reducing agent in a second continuous microreactor to form a stable alcohol, or a stable aldehyde or ketone, optionally protected as the hydrate, hemiacetal or acetal.

5. The multi-step process according to claim 1, wherein step c) is a hydrogenation step.

6. The multi-step process according to claim 2, wherein step b) is a hydrogenation step.

7. The multi-step process according to claim 1, wherein step a) and b) are performed in a continuous microreactor in a homogeneous solution or in a continuous liquid/liquid microreactor and wherein step c) is performed in a gas/liquid microreactor.

8. The multi-step process according to claim 2, wherein step a) is performed in a continuous microreactor in a homogeneous solution or in a continuous liquid/liquid microreactor and wherein step b) is performed in a gas/liquid microreactor.

9. The multi-step process according to claim 3, wherein step a) and b) are performed in a continuous microreactor in a homogeneous solution, in a continuous liquid/liquid microreactor or in a continuous gas/liquid microreactor and wherein step c) is performed in a gas/liquid microreactor.

10. The multi-step process according to claim 4, wherein step a) is performed in a continuous microreactor in a homogeneous solution, in a continuous gas/liquid or in a continuous liquid/liquid microreactor and wherein step b) is performed in a gas/liquid microreactor.

11. The multi-step process according to claim 4 wherein step a) and step b) are performed in a gas/liquid microreactor.

12. The multi-step process according to claim 1, wherein step c) is performed in a gas/liquid microreactor with an immobilized catalyst.

13. The multi-step process according to claim 2, wherein step b) is performed in a gas/liquid microreactor with an immobilized catalyst.

14. The multi-step process according to claim 4, wherein step a) comprises performing a reaction of naphthalene with ozone in a gas/liquid microreactor, and wherein step b) comprises reducing the hazardous peroxo intermediate to o-phthalic aldehyde in a second microreactor.

15. The multi-step process according to claim 14, wherein step b) comprises performing the reduction of the hazardous peroxo intermediate by hydrogenation in a gas/liquid microreactor with an immobilized catalyst.

16. The multi-step process according to claim 3, wherein the reaction of step a) is performed in a combustible solvent.

* * * * *